United States Patent [19]
Ueno et al.

[11] Patent Number: 5,218,387
[45] Date of Patent: Jun. 8, 1993

[54] EYE POSITION DETECTING APPARATUS

[75] Inventors: Hiroshi Ueno, Yokohama; Kazuhiko Yoshida, Yokosuka, both of Japan

[73] Assignee: Nissan Motor Co., Ltd., Yokohama, Japan

[21] Appl. No.: 703,114

[22] Filed: May 20, 1991

[30] Foreign Application Priority Data

May 21, 1990 [JP] Japan ................. 2-129274

[51] Int. Cl.⁵ .............. A61B 3/113; G06F 15/42
[52] U.S. Cl. .............. 351/210; 364/413.02; 364/DIG. 2; 364/922.3
[58] Field of Search .............. 351/209, 210, 246; 356/214, 380; 359/201, 202; 364/922, 922.2, 922.3, 922.4, DIG. 2, 413.02

[56] References Cited

U.S. PATENT DOCUMENTS

| | | | |
|---|---|---|---|
| 4,169,663 | 10/1979 | Murr | 351/210 |
| 4,528,989 | 7/1985 | Weinblatt | 351/210 X |
| 4,720,189 | 1/1988 | Heynen et al. | 351/210 |
| 4,836,670 | 6/1989 | Hutchinson | 351/210 |

FOREIGN PATENT DOCUMENTS 60-158303  1/1984  Japan .
60-158304  1/1984  Japan .
61-77705   9/1984  Japan .
61-77706   9/1984  Japan .
62-247410 12/1985  Japan .

Primary Examiner—Bruce Y. Arnold
Assistant Examiner—David Parsons
Attorney, Agent, or Firm—Lowe, Price, LeBlanc & Becker

[57] ABSTRACT

An image of a face including eyes is converted into a binary coded image. The binary coded image is processed to detect first and second rectangular regions including image portions representing the eyes, respectively. For this purpose, the binary coded image is scanned in a series of horizontal scan lines to detect the X and Y coordinates of initial and final pixels of a line segment representing the longest width of the face. The X coordinates of each of the first and second rectangular regions are calculated based upon the detected X coordinates of the initial and final pixels. An image portion above the line segment is scanned to detect the Y coordinate of a lowermost one of pixels forming black image portions. The Y coordinates of the first and second rectangular regions are calculated based upon the detected Y coordinate of the lowermost pixel.

36 Claims, 9 Drawing Sheets

EYE POSITION DETECTING APPARATUS

BACKGROUND OF THE INVENTION

This invention relates to an eye position detecting apparatus for detecting eye positions in an image of a face.

For example, Japanese Patent Kokai Nos. 60-158303, 60-158304, 61-77705 and 61-77706 disclose eye position detecting apparatus for detecting driver's eye positions in order to check a driver's doze and inattentive driving. These apparatus employ two images of a driver's face. The first image is obtained with infrared rays irradiated to the driver's face in one direction and the second image is obtained with infrared rays irradiated to the driver's face in another direction. These two images are processed to detect the positions of specified points different from the circumference. The detected positions are utilized to recognize the three-dimensional positions of the driver's eyes. One serious problem with such eye position detecting apparatus is the shadows of the hair, eyebrows and spectacle frame on the images which may dissolve the specified points.

SUMMARY OF THE INVENTION

Therefore, it is a main object of the invention to provide an improved eye position detecting apparatus which can detect eye positions with higher accuracy.

There is provided, in accordance with the invention, an eye position detecting apparatus comprising image input means for inputting an image of a face including eyes, image converting means for converting the inputted image into a binary coded image formed by an array of pixels having a first value indicating a black pixel or a second value indicating a white pixel, each of the pixels being located at a position specified by coordinates (X,Y), and detecting means for processing the binary coded image to detect first and second rectangular regions including image portions representing the eyes, respectively, each of the first and second rectangular regions being specified by two X coordinates and two Y coordinates. The detecting means includes first means for scanning the binary coded image in a series of horizontal scan lines to detect the X and Y coordinates of initial and final pixels of a line segment representing the longest width of the face, second means for calculating the X coordinates of each of the first and second rectangular regions based upon the detected X coordinates of the initial and final pixels, third means for scanning an image portion above the line segment to detect the Y coordinate of a lowermost one of pixels forming black image portions, and fourth means for calculating the Y coordinates of the first and second rectangular regions based upon the detected Y coordinate of the lowermost pixel.

BRIEF DESCRIPTION OF THE DRAWINGS

This invention will be described in greater detail by reference to the following description taken in connection with the accompanying drawings, in which.

DETAILED DESCRIPTION OF THE INVENTION

Figure 1:
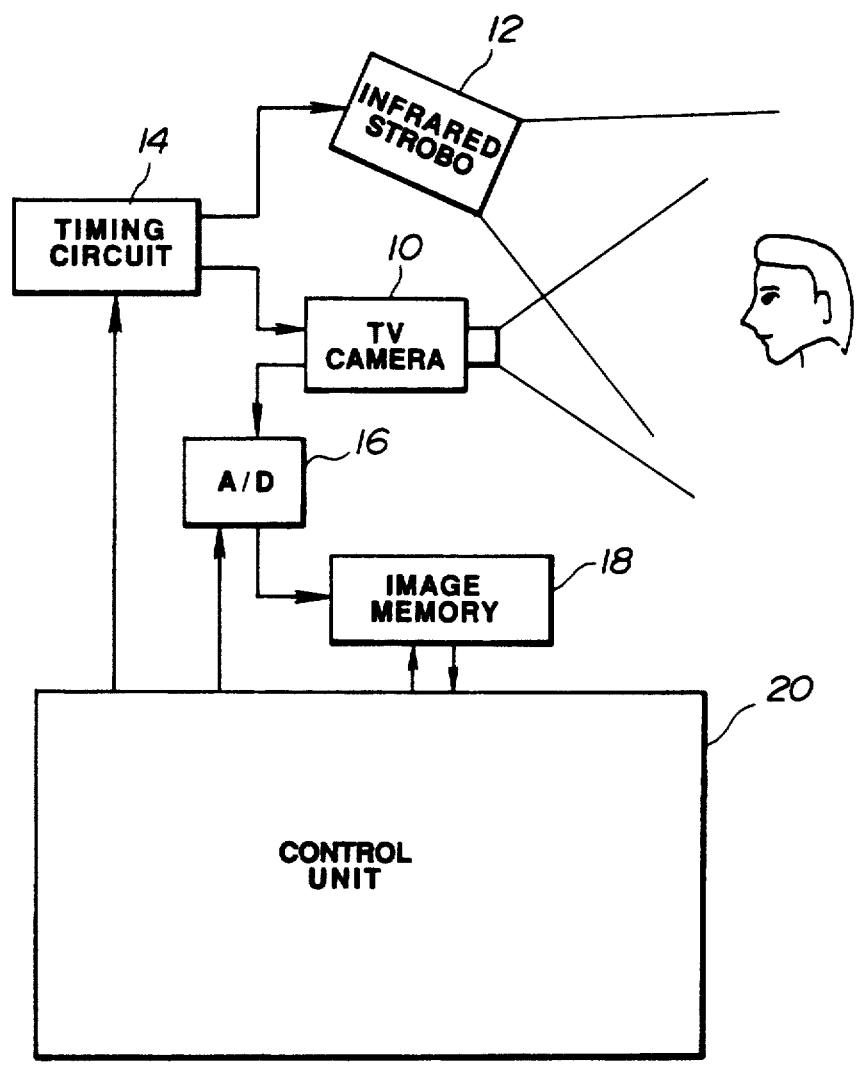
FIG. 1 is a schematic diagram showing one embodiment of an eye position detecting apparatus made in accordance with the invention.
Figure 2:
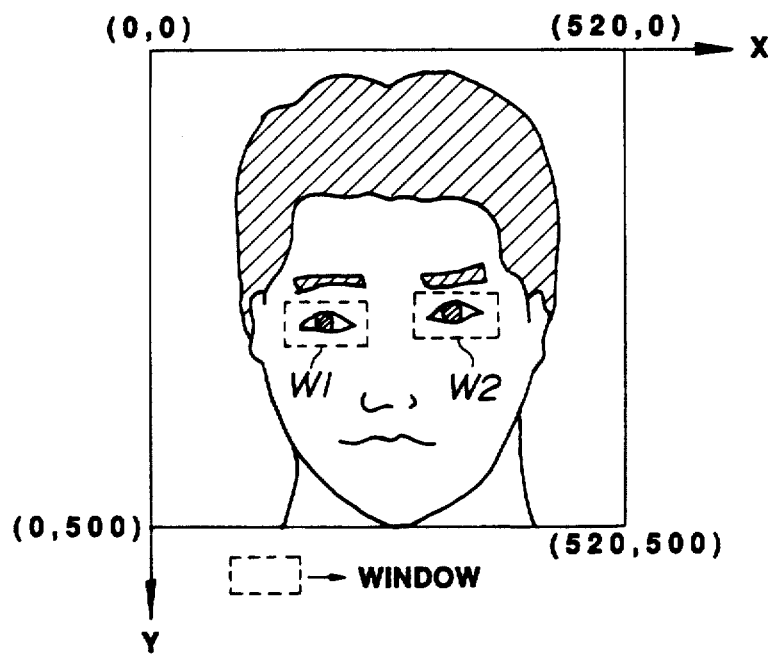
FIG. 2 is a diagram showing an inputted image of a driver's face.

With reference to the drawings, and in particular to FIG. 1, there is shown an eye position detecting apparatus embodying the invention. The eye position detecting apparatus comprises a television camera 10, an infrared stroboscopic flash 12, a timing circuit 14, an analog-to-digital converter 16, and a one-frame image memory 8. The television camera 10 and the infrared stroboscopic flash 12 are provided on an instrument panel located in front of a driver seat. The television camera 10 is focused on a driver's face to which infrared rays are irradiated from the infrared stroboscopic flash 12. The A/D converter 16 receives a video signal from the television camera 10 and converts it into digital form having 256 (0 to 255) tones for application to the image memory 24 which digitally stores an image of the driver's face represented by a 520×500 array of picture elements or pixels, as shown in FIG. 2. Each pixel I(X,Y) is assigned a value representative of its intensity (darkness). In FIG. 2, first and second rectangular regions or windows W1 and W2 are shown as containing image portions representing the driver's left and right eyes, respectively.

The eye position detecting apparatus also comprises a control unit 20 which controls the timing circuit 14, the A/D converter 16 and the image memory 18. The control unit 20 produces an image input command to the A/D converter 16 and the image memory 18 so that the image memory 18 stores an image of the driver's face. The control unit 20 also produces a command causing the timing circuit 14 to actuate the infrared stroboscopic flash 12 in synchronism with the image input command. The control unit 20 processes the image stored in the image memory 18 to detect the driver's eye positions, the driver's iris center positions and a driver's doze or inattentive driving. The control unit 20 may employ a digital computer which includes a central processing unit, a random access memory, a read only memory, buffers, counters and an input/output control circuit.

Figure 3:
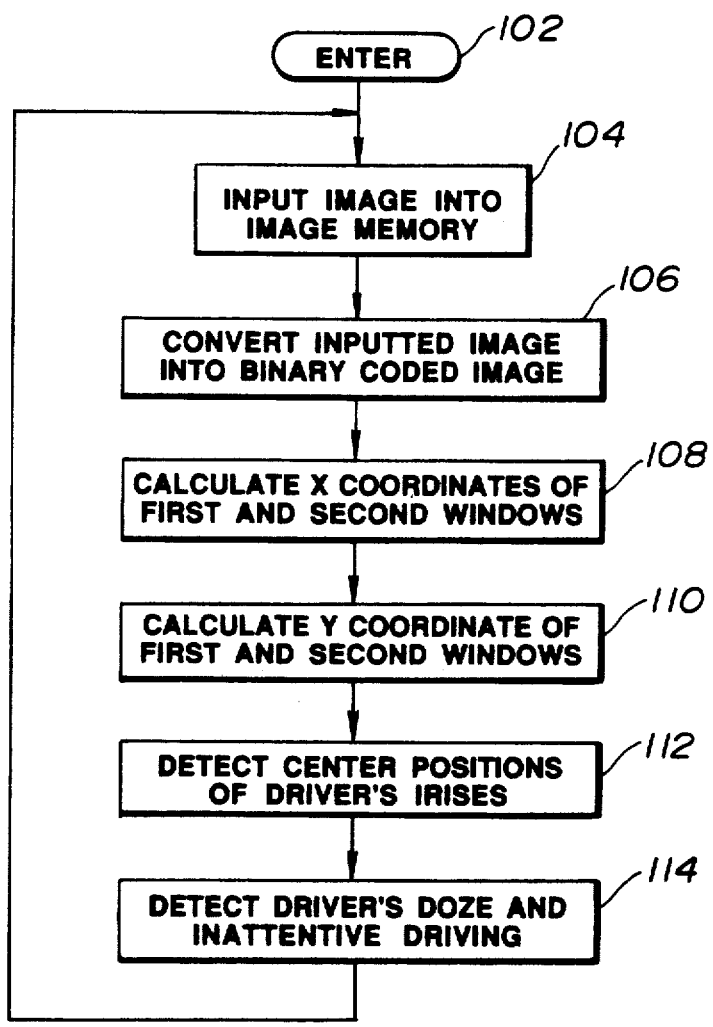
FIG. 3 is an overall flow diagram of the programming of the digital computer used in the control unit of FIG. 1.

FIG. 3 is an overall flow diagram of the programming of the digital computer used in the control unit 20. The computer program is entered at the point 102. At the 104 in the program, commands are produced to store an image of the driver's face in the one-frame image memory 18. The image memory 18 digitally stores an image of the driver's face represented by a 520×500 array of picture elements or pixels. Each pixel I(X, Y) is assigned a value representative of its intensity (darkness). At the point 106 in the program, the inputted image is converted into a binary coded image formed by a 520×500 array of pixels. Each pixel J(X<Y) has a binary value of 0 or 1. Thus, J(X, Y)=1 represents a black pixel, while J(X, Y)=0 represents a white pixel. This conversion is made by comparing the pixel I(X, Y) with a threshold value. This is effective to provide a driver's face image having a sharp contrast between the light and shade areas thereof. The threshold value is selected to ensure the extraction of the image portions of the respective driver's eyes.

At the point 108 in the program, the binary coded image is scanned in a series of raster scan lines to detect the X and Y coordinates of initial and final pixels of a line segment representing the longest width of the driver's face. The detected X coordinates are used to calculate the X coordinates X1 and X2 of the first window W1 and the X coordinates XX1 and XX2 of the second window W2. At the point 110 in the program, an image portion above the line segment is scanned in a series of vertical scan lines to detect the Y coordinate of a lowermost one of pixels forming black image portions. The detected Y coordinate is used to calculate the Y coordinates of the first and second windows W1 and W2.

At the point 112 in the program, the positions of the centers of the respective driver's irises are detected. At the point 114 in the program, a driver's doze or inattentive driving is detected. Following this, the program is returned to the point 104.

Figure 4:
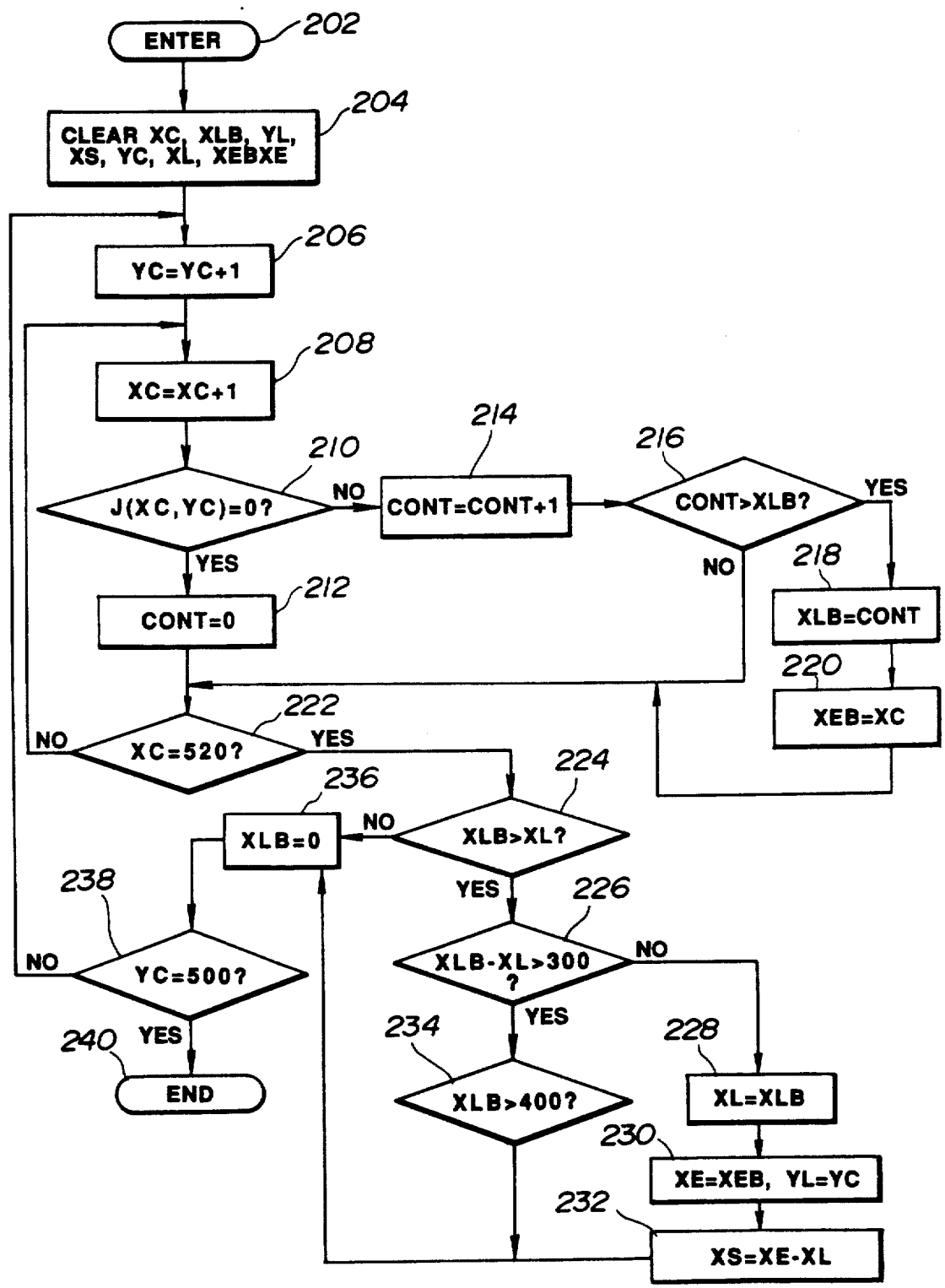
FIG. 4 is a flow diagram of the programming of the digital computer as it is used to detect the longest width of the driver's face.

FIG. 4 is a flow diagram of the programming of the digital computer as it is used to detect the longest width of the driver's face from the contour of the driver's face. The digital computer processes the binary coded image from left-to-right and from top-to-bottom to serialize a 520×500 array of pixels in a raster scan sequence J(1,1), J(2,2), ..., J(520,1), J(1,2), J(2,2), ... J(520,2), ..., J(520,500). The digital computer employs X and Y counters to represent the coordinates (XC,YC) specifying an existing pixel J(XC,YC) which is judged to be a white or black pixel. The digital computer also employs a consecutive white pixel counter COUNT to count the number of consecutive white pixels which form a white line segment extending along one horizontal scan line. The counted number is stored in a first buffer XLB. The X coordinate of the final white pixel of the white line segment is stored in a second buffer XEB. This process is repeated from the first horizontal scan line (YC=1) to the last horizontal scan line (YC=500) to detect a longest white line segment formed by a greatest number XL of consecutive white pixels. This longest white line segment indicates the width of the driver's face. The greatest number XL is stored in the computer memory. The ending coordinate XE of the longest white line segment is stored in the computer memory. The starting coordinate XS of the longest white line segment is calculated as XS=XE−XL and stored in the computer memory. The Y coordinate YL of the longest white line segment is also stored in the computer memory.

The computer program is entered at the point 202. AT the point 204 in the program, the X and Y counters are reset to zero, the first and second buffers XLB and XEB are cleared to zero, and the values XL, XE, XS and YL are cleared to zero. At the point 206 in the program, the Y counter is incremented by one step. The program then proceeds to the point 208 where the X counter is incremented by one step. At the point 210 in the program, a determination is made as to whether or not the existing pixel J(XC,YC), which is represented by the coordinates (XC,YC) corresponding to the counts XC and YC of the X and Y counters, has a binary value of 0. If the answer to this question is "yes", then it means that the existing pixel J(XC,YC) is a black pixel and the program proceeds to the point 212 where the consecutive white pixel counter CONT is cleared to zero. The program then proceeds from the point 212 to the point 222.

If the answer to the question inputted at the point 210 is "no", then it means that the existing pixel J(XC,YC) is a white pixel and the program proceeds to the point 214 where the consecutive white pixel counter CONT is incremented by one step. The program then proceeds from the point 214 to a determination step at the point 216. This determination is as to whether or not the count of the consecutive white pixel counter CONT is greater than the value stored in the first buffer XLB. If the answer to this question is "no", then the program proceeds to the point 222. Otherwise, the program proceeds from the point 216 to the point 218 where the count of the consecutive white pixel counter CONT is used to update the value stored in the first buffer XLB. The program then proceeds to the point 220 where the existing count XC of the X counter is used to update the value stored in the second buffer XBE. Following this, the program proceeds to the point 222.

At the point 222 in the program, a determination is made as to whether or not the count XC of the X counter is equal to 520. If the answer to the question is "no", then the program is returned to the pint 208 where the X counter is incremented by one step. Otherwise, it means that all of the pixels arranged along one horizontal scan line have been processed and the program proceeds to another determination step at the point 224. This determination is as to whether or not the value stored in the first buffer XLB is greater than a maximum value XL stored in the computer memory. If the answer to this question is "no", then the program proceeds to the point 236. Otherwise, the program proceeds to another determination step at the point 226. This determination is as to whether or not the difference (XLB−XL) of the maximum value XL from the value XLB stored in the first buffer XLB is greater than a predetermined value, in the illustrated case 300. If the answer to this question is "no", then the program proceeds to the point 228 where the value XLB stored in the first buffer XLB is used to update the maximum value XL. The program then proceeds to the point 230 where the value XEB stored in the second buffer XEB is used to update the ending coordinate XE and the existing Y coordinate YC is used to update the value YL stored in the computer memory. The program then proceeds to the point 232 where the starting coordinate XS is calculated as XS=XE−XL. Following this, the program proceeds to the point 236.

If the answer to the question inputted at the point 226 is "yes", then it means that a great or rapid change occurs in the length of the white line segment formed by the continuous white pixels and the program proceeds to another determination step at the point 234. This determination is as to whether or not the value XLB is greater than a predetermined value, in the illustrated case 400. If the answer to this question is "yes", it means that an error occurs and the program proceeds to the point 236. Otherwise, the program proceeds to the point 228.

At the point 236 in the program, the value XLB of the first buffer XLB is cleared to zero. The program then proceeds from the point 236 to the point 238. At the point 238, a determination is made as to whether or not the count YC of the Y counter is equal to 500. If the answer to this question is "no", then the program is returned to the point 206. Otherwise, the program proceeds to the end point 240.

The values XL, YL, XE and XS stored eventually in the computer memory are used to determine the X coordinates of the first and second windows W1 and W2. That is, the X coordinates X1 and X2 of the first window W1 is given as $X1=XS$ and $X2=Xc-25$ and the X coordinates XX1 and XX2 of the second window W2 is given as $XX1=Xc+25$ and $XX2=XE$ where Xc is the X coordinate of the center of the longest white line segment and is given as $Xc=XS+\{(XE-XS)/2\}$.

Figure 5A:
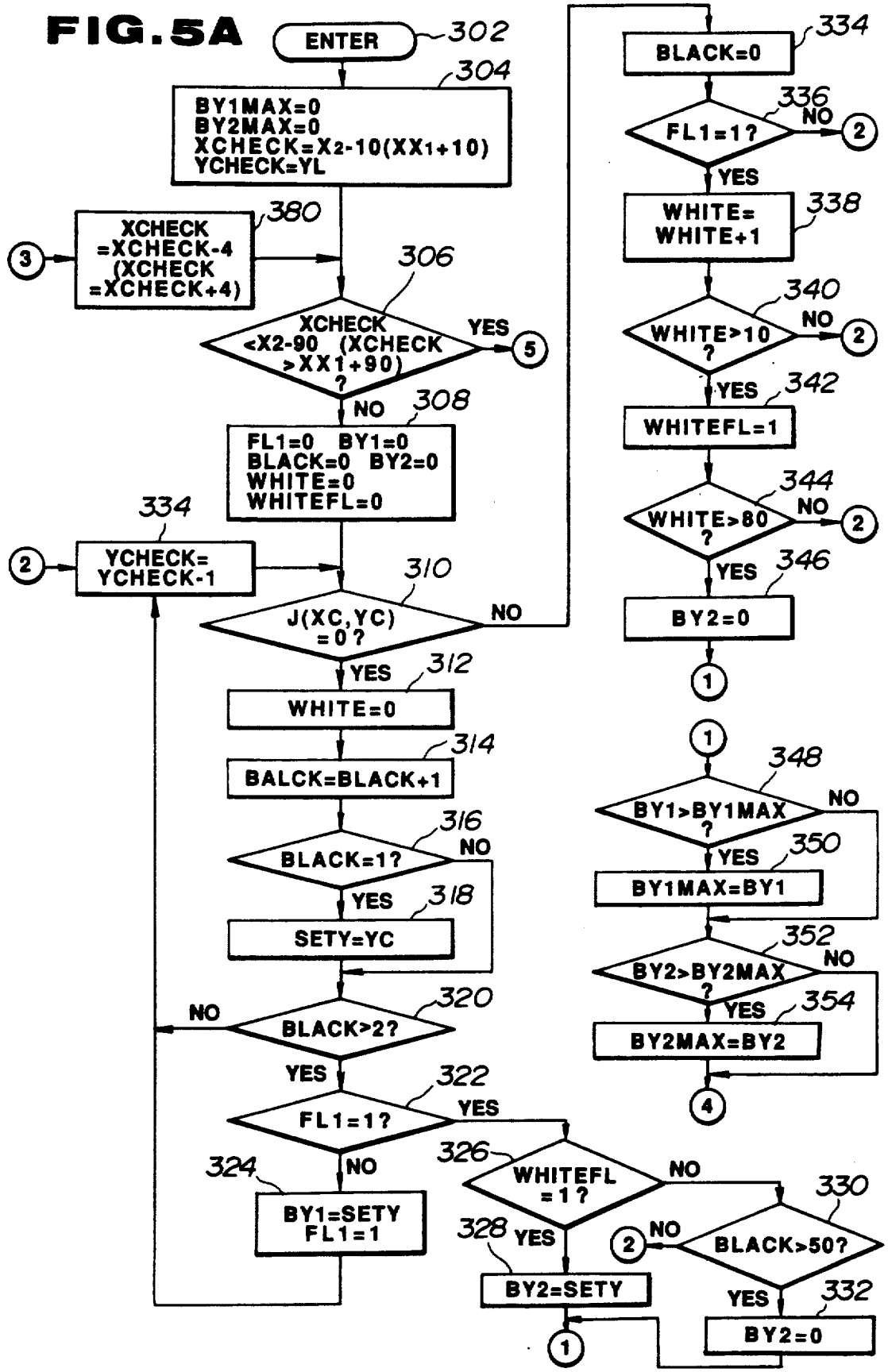
FIGS. 5A and 5B are flow diagrams of the programming of the digital computer as it is used to detect the Y coordinates of the first and second rectangular regions including image portions representing the driver's eyes, respectively.
Figure 5B:
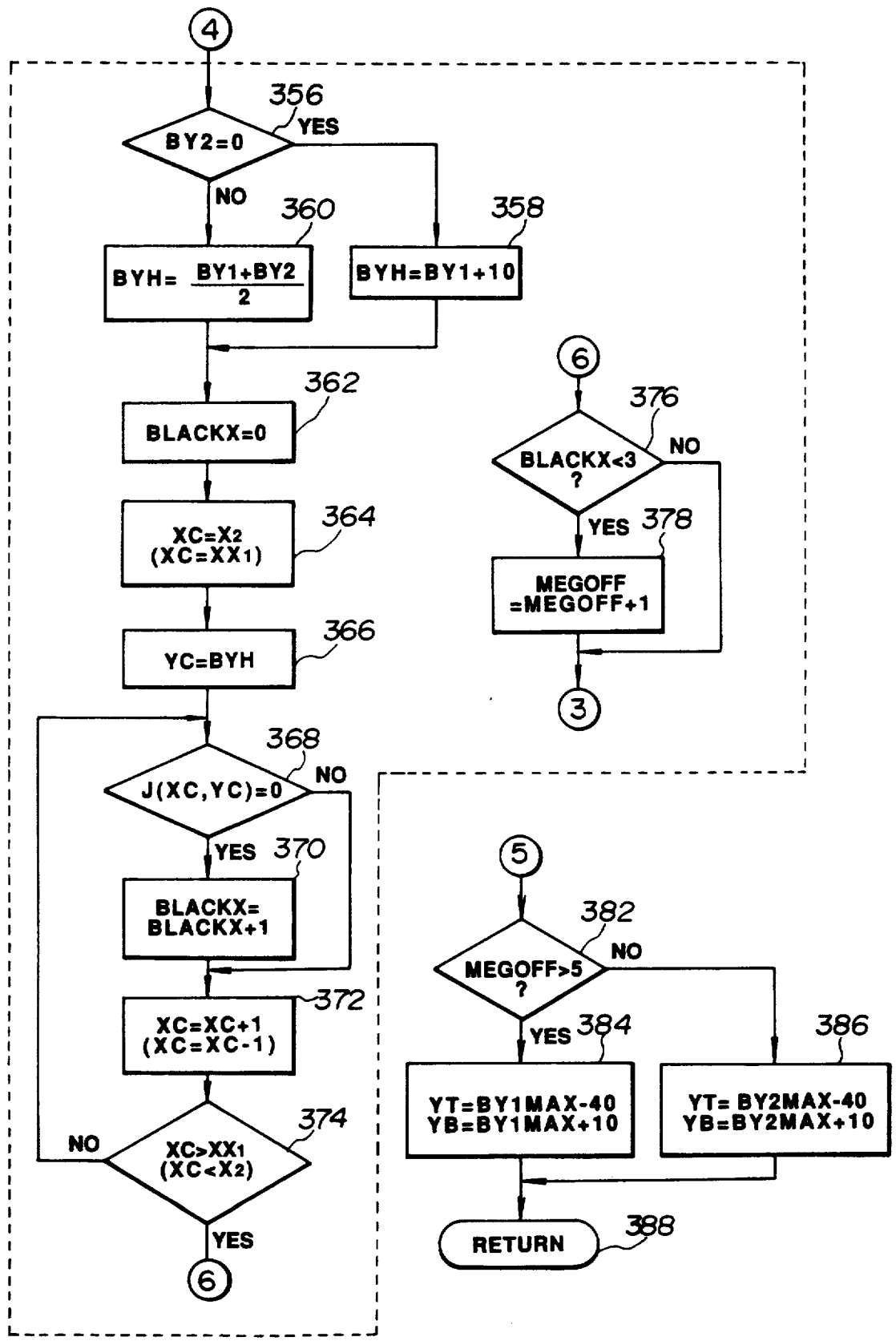
Figure 6:
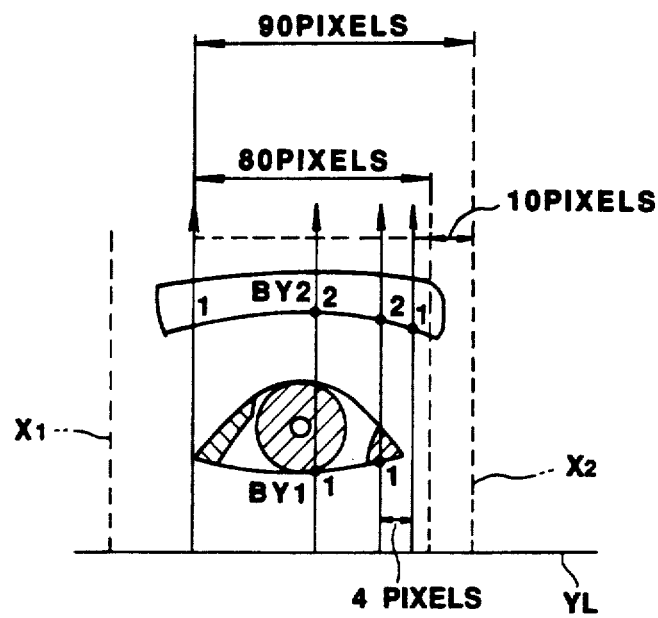
FIG. 6 is a diagram used in explaining the process of detecting the Y coordinates of the first and second rectangular regions.

FIGS. 5A and 5B are flow diagrams of the programming of the digital computer as it is used to detect the Y coordinates of the first and second windows W1 and W2. The binary coded image is scanned upward in a series of vertical scan lines over the ranges $(X2-90) \leq X \leq (X2-10)$ and $0 \leq Y \leq YL$ to detect the Y coordinate of the lowermost one of pixels forming black image portions for the first window W1, as shown in FIG. 6, and over the range $(XX1+10) \leq X \leq (XX1+90)$ and $0 \leq Y \leq YL$ to detect the Y coordinate of the lowermost one of pixels forming black image portions for the second window W2. These ranges are effective to avoid the black image portions indicating the driver's nostrils. It is preferable to shorten the image processing time required to detect the Y coordinates of the first and second windows W1 and W2 by arranging the vertical scan lines for every predetermined number of (in the illustrated case 4) pixels.

The computer program is entered at the point 302. At the point 304 in the program, the values BY1MAX and BY2MAX are cleared to zero, the counter XCHECK is reset to $(X2-10)$ for the first window W1 or to $(XX1+10)$ for the second window W2, and the counter YCHECK is reset to YL. At the point 306 in the program, a determination is made as to whether or not the count of the counter XCHECK is less than $(X2-90)$ for the first window W1 or greater than $(XX1+90)$ for the second window W2. If the answer to this question is "yes", then it means that this process has been completed and the program proceeds to the point 382. Otherwise, the program proceeds to the point 308 where the flags FL1 and WHITEFL are cleared to zero, the buffers BY1 and BY2 are cleared to zero, and the the consecutive black and white pixel counters BLACK and WHITE are reset to zero. At the point 310 in the program, a determination is made as to whether or not the existing pixel J(XC, YC), which is represented by the coordinates (XC, YC) corresponding to the counts XC and YC of the counters XCHECK and YCHECK, has a binary value of 0. If the answer to this question is "yes", then it means that the existing pixel J(XC, YC) is a black pixel and the program proceeds to the point 312 where the consecutive white pixel counter WHITE is cleared to zero. The program then proceeds to the point 314 where the consecutive black pixel counter BLACK is incremented by one step. Following this, the program proceeds to a determination step at the point 316. This determination is as to whether or not the count of the consecutive black pixel counter BLACK is equal to 1. If the answer to this question is "yes", then it means that the existing pixel J(XC, YC) is the first black pixel on the vertical scan line $X=XC$ and the program proceeds to the point 318 where the existing Y coordinate YC, which is indicated by the count of the counter YCHECK, is stored in the buffer SETY. For example, the value stored in the buffer SETY is the Y coordinate of one of the pixels indicated by the numeral 1 in FIG. 6. The value stored in the buffer SETY indicates a candidate for the lowermost Y coordinate of one of lower and upper black area portions. Following this, the program proceeds to the point 320. If the answer to the question inputted at the point 316 is "no", then the program proceeds directly to the point 320.

At the point 320 in the program, a determination is made as to whether or not the count of the consecutive black pixel counter BLACK is equal to or greater than 2. If the answer to this question is "no", then the program proceeds to the point 334 where the counter YCHECK is decremented by one step. Following this, the program is returned to the point 310 for the process for the next, upper pixel J(XC, YC). If the count of the consecutive black pixel counter BLACK is greater than 2, then the program proceeds from the point 320 to another determination step at the point 332. This determination is as to whether or not the flag FL1 is set. If the answer to this question is "yes", then the program proceeds to the point 326. Otherwise, the program proceeds to the point 324 where the flag FL1 is set to indicate that one of lower and upper black image portions has been detected and the value stored in the buffer SETY is stored in the buffer BY1. Following this, the program proceeds to the point 334.

If the answer to the question inputted at the point 322 is "yes", then the program proceeds to another determination point 326. This determination is as to whether or not the flag WHITEFL has been set to indicate that ten or more white pixels have been continued. If the answer to this question is "yes", then it means that the detected black image portion is the upper black image portion and the program proceeds to the point 328 where the value stored in the buffer SETY is stored in the buffer BY2. (For example, the value stored in the buffer BY2 is the Y coordinate of one of the pixels indicated by the numeral 2 in FIG. 6. Following this, the program proceeds to the point 348. If the answer to the question inputted at the point 326 is "no", then it means that a small or indistinct distance exists between the lower and upper black image portions and the program proceeds to another determination step at the point 330. This determination is as to whether or not the count of the consecutive black pixel counter BLACK is greater than 50. If the answer to this question is "yes", then it mean that the existing black pixel forms a part of the driver's hair and the program proceeds to the point 332 where the buffer BY2 is cleared to zero. Following this, the program proceeds to the point 348.

If the answer to the question inputted at the point 310 is "no", then it means that the existing pixel J(XC, YC) is a white pixel and the program proceeds to the point 334 where the consecutive black pixel counter BLACK is reset to zero. The program then proceeds to a determination step at the point 336. This determination is as to whether or not the flag FL1 has been set. If the answer to this question is "no", then it means that no black image portion has been detected and the program proceeds to the point 334. Otherwise, the program proceeds to the point 338 where the consecutive white pixel counter WHITE is incremented by one step. The program then proceeds to the point 340 where a determination is made as to whether or not the count of the consecutive white pixel counter WHITE is equal to or greater than 10. If the answer to this question is "no", then the program proceeds to the point 334. Otherwise, the program proceeds to the point 342 where the flag WHITEFL is set to indicates that the existing pixel J(XC, YC) forms a part of a white image portion between the eye and the eyebrow or a white image portion between the eye and the spectacle frame. The program then proceeds to the point 344 where a determination is made as to whether or not the count of the consecutive white pixel counter WHITE is equal to or greater than 80. If the answer to this question is "yes", then it means that the existing pixel J(XC, YC) is on a vertical scan line which does not intersect the driver's eyebrow and the program proceeds to the point 346 where the buffer BY2 is cleared to zero and then proceeds to the point 348. Otherwise, the program proceeds to the point 334.

At the point 348 in the program, a determination is made as to whether or not the value stored in the buffer BY1 is greater than a maximum value BY1MAX stored in the computer memory. If the answer to this question is "yes", then it means that the pixel whose Y coordinate is stored in the buffer BY1 is the lowermost black pixel and the program proceeds to the step 350 where the value of the buffer BY1 is used to update the value BY1MAX stored in the computer memory. The maximum value BY1MAX is eventually equal to an maximum value which indicates the Y coordinate of the lowermost one of the black pixels forming the lower black image portion. The program then proceeds to the point 352. If the answer to the question inputted at the point 348 is "no", then the program proceeds directly to the point 352. At the point 352 in the program, a determination is made as to whether or not the value stored in the buffer BY2 is greater than a maximum value BY2MAX stored in the computer memory. If the answer to this question is "yes", then the program proceeds to the step 354 where the value stored in the buffer BY2 is used to update the maximum value BY2MAX stored in the computer memory. The maximum value BY2MAX is eventually equal to a maximum value which indicates the Y coordinate of the lowermost one of the black pixel forming the upper black image portion. The program then proceeds to the point 356. If the answer to the question inputted at the point 352 is "no", then the program proceeds directly to the point 356.

Figure 7:
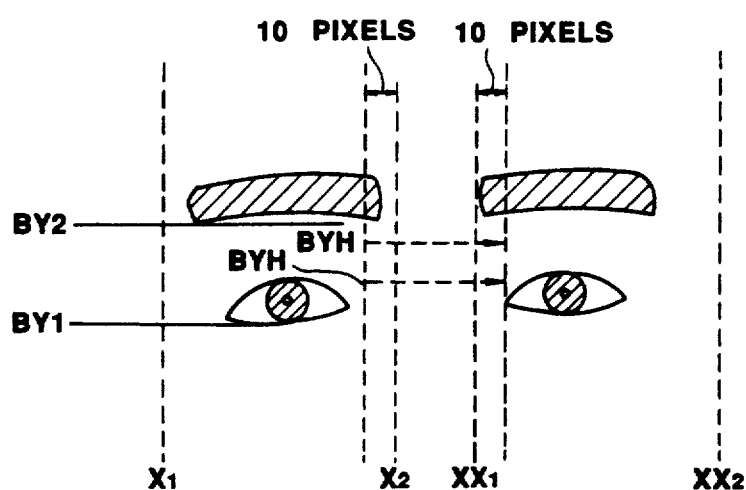
FIG. 7 is a diagram used in explaining the process of detecting the presence of a spectacle frame.

At the point 356 in the program, a determination is made as to whether or not the value stored in the buffer BY2 is zero. If the answer to this question is "yes", then it means that the upper black image portion has not been detected and the program proceeds to the point 358. At the point 358 in the program, the Y coordinate BYH (FIG. 7) of a horizontal scan line for detecting the spectacle frame is calculated as BYH = BY1 + 10 where BY1 is the value stored in the buffer BY1. Following this, the program proceeds to the point 362. If the answer to the question inputted at the point 356 is "no", then the program proceeds to the point 360 where the Y coordinate BYH (FIG. 7) of the horizontal scan line for detecting the spectacle frame is calculated as BYH = -(BY1 + BY2)/2 where BY1 is the value stored in the buffer BY1 and BY2 is the value stored in the buffer BY2. Although the Y coordinate BYH is calculated as the center of the Y coordinates BY1 and BY2, it is to be noted that the BYH may be any one of the Y coordinates between the Y coordinates BY1 and BY2. Following this, the program proceeds to the point 362.

At the point 362 in the program, the black pixel counter BLACKX is cleared to zero. Following this, the program proceeds to the point 364 where the X counter is set to its initial value X2 for the first window W1 or to its initial value XX1 for the second window W2. The program then proceeds to the point 366 where the Y counter is set to the value BYH calculated at the point 358 or 360. The program then proceeds to a determination step at the point 368. This determination is as to whether or not the existing pixel J(XC, YC), which is represented by the coordinates (XC,YC) corresponding to the counts of the X and Y counters, has a binary value of 0. If the answer to this question is "yes", then it means that the pixel J(XC, YC) is a black pixel and the program proceeds to the point 370 where the black pixel counter BLACKX is incremented by one step and then to the point 327. Otherwise, the program proceeds directly to the point 372.

At the point 372 in the program, the X counter is incremented by one step for the first window W1 or decremented by one step for the second window W2. The program then proceeds to a determination step at the point 374. This determination is as to whether or not the count of the X counter is greater than XX1 for the first window W1 or less than X2 for the second window W2. If the answer to this question is "yes", then it means that this process has been completed for all of the pixels arranged on the horizontal scan line Y = BYH and the program proceeds to the point 376. Otherwise, the program is returned to the point 368.

At the point 376 in the program, a determination is made as to whether or not the count of the black pixel counter BLACKX is less than 3. If the answer to this question is "yes⇌", then the program proceeds to the point 378 where a counter MEGOFF is incremented. Following this, the program proceeds to the point 380. If the count of the black pixel counter BLACKX is equal to or greater than 3, then the program proceeds from the point 376 directly to the point 380.

At the point 380 in the program, the counter XCHECK is decremented by four steps for the first window W1 or incremented by four steps for the second window W2. Thus, the process is performed for the next vertical scan line.

If the process has been completed for all of the pixels in the specified ranges, the program proceeds from the point 306 to the point 382. At the point 382, a determination is made as to whether or not the count of the counter MEGOFF is greater than 5. If the answer to this question is "yes", then it means that the driver wears no spectacles and the program proceeds to the point 384. At the point 384 in the program, the Y coordinates YT and YB of the first and second windows W1 and W2 are calculated as YT = BY1MAX − 40 and YB = BY1MAX + 10 where BY1MAX is the Y coordinate of the lowermost one of the pixels forming the lower black image portion. Following this, the program proceeds to the point 388 where the program is returned to the entry point 302. If the count of the counter MEGOFF is equal to or less than 5, then it means that the center portion of the spectacle frame is detected and the program proceeds from the point 382 to the point 386. At the point 386 in the program, the Y coordinates YT and YB of the first and second windows W1 and W2 are calculated as YT=BY2MAX−40 and YB=BY2MAX+10 where BY2MAX is the Y coordinate of the lowermost one of the pixels forming the upper black image portion. Following this, the program proceeds to the point 388.

Figure 8:
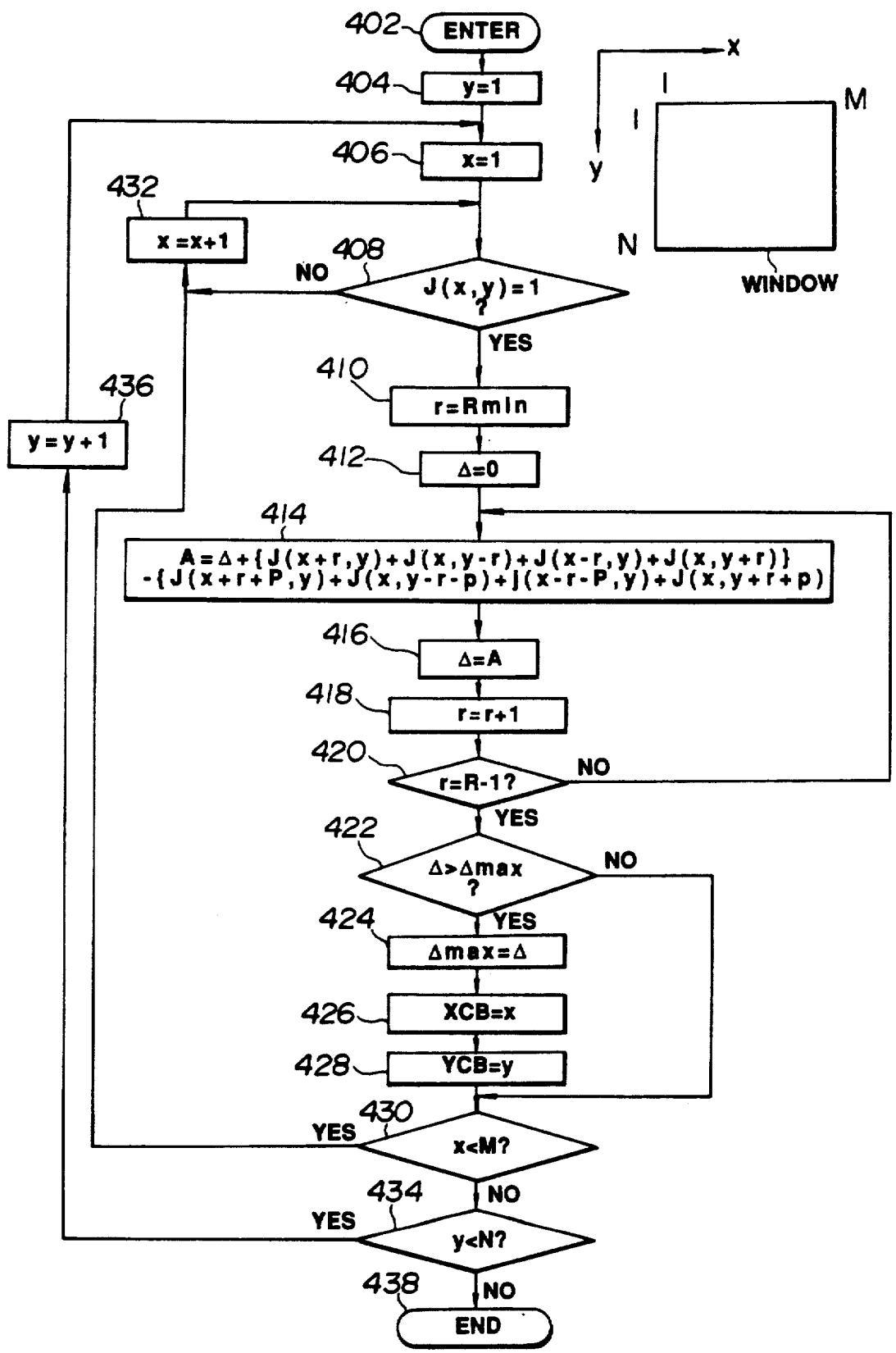
FIG. 8 is a flow diagram of the digital computer as it is used to detect driver's iris center positions.
Figure 9:
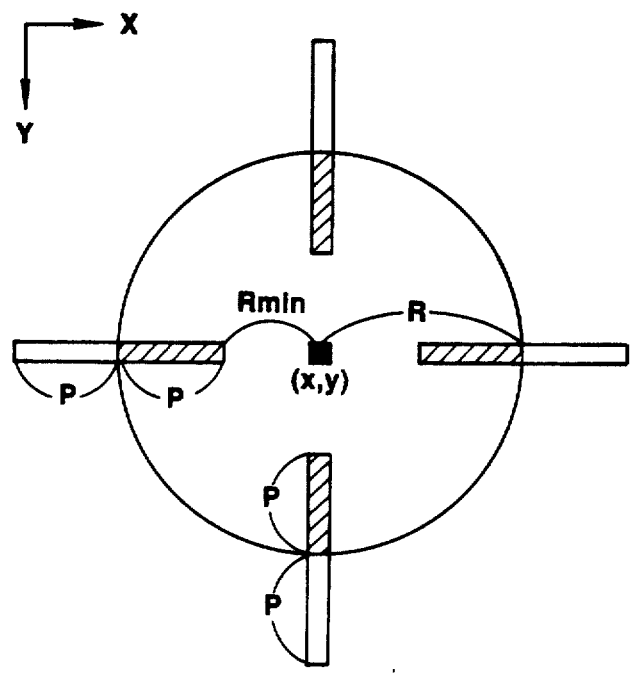
FIG. 9 is a diagram used in explaining the principles of the driver's iris center position detection.

FIG. 8 is a flow diagram of the programming of the digital computer as it is used to detect the center position of each of the driver's irises. The digital computer scans each of the rectangular windows W1 and W2 formed by an M×N array of pixels in a series of raster scan lines. A circle with its center positioned at a pixel J(x,y) and with a radius of R is considered along with four radial line segments each divided by the circle into inner and outer portions having the same length P, as shown in FIG. 9. A difference between the sum of the values of the pixels located on the inner portions, indicated by the hatched areas of FIG. 9, and the sum of the values of the pixels located on the outer portions is calculated. This calculation is made for all of the pixels J(x,y) positioned in the rectangular window to detect a maximum value of the calculated differences. If the difference calculated for a pixel is at maximum, the pixel will form the center of the driver's iris.

The computer program is entered at the point 402. At the point 404 in the program, the y counter is set to 1. At the point 406 in the program, the x counter is set to 1. The program then proceeds to a determination step at the point 408. This determination is as to whether or not the existing pixel J(x,y), represented by the coordinate (x,y) corresponding to the counts of the x and y counters, has a binary value of 1. If the answer to this question is "no", then it means that the existing pixel is a white pixel and the program proceeds to the point 432 where the x counter is incremented by one step and then to the point 408. Otherwise, the program proceeds to the point 410 where the r counter is set to Rmin (FIG. 9). The program then proceeds to the point 412 where the Δ buffer is cleared to zero. The program then proceeds to the point 414 where a difference A is calculated as
$A=\Delta+\{J(x+r,y)+J(x,y-r)+J(x-r,y)+J(x,y+r)\}-\{J(x+r+P,y)+J(x,y-r-P)+J(x-r-P,y)+J(x,y+r+P)\}$.

At the point 416 in the program, the calculated value is used to update the value stored in the Δ buffer. The program then proceeds to the point 418 where the r counter is incremented by one step. The program then proceeds to a determination step at the point 420. This determination is as to whether or not the count of the r counter is equal to a maximum value (R−1). If the answer to the question is "yes", then it means that the process has been completed for the pixel J(x,y) and the program proceeds to the point 422. Otherwise, the program is returned to the point 414.

At the point 422 in the program, a determination is made as to whether or not the count of the Δ buffer is greater than a maximum value Δ max stored in the computer memory. If the answer to the question is "yes", then the program proceeds to the point 424 where the count of the Δ buffer is used to update the maximum value Δ max stored in the computer memory. The program then proceeds to the point 426 where the count of the x counter is used to update a value stored in the buffer XCB and then to the point 428 where the count of the y counter is used to update a value stored in the buffer YCB. Following this, the program proceeds to the point 430. If the answer to the question inputted at the point 422 is "no", then the program proceeds directly to the point 430.

At the point 430 in the program, a determination is made as to whether or not the count of the x counter is less than M. If the answer to this question is "yes", then the program proceeds to the point 432 where the x counter is incremented by one step and then to the point 408. Otherwise, the program proceeds to another determination step at the point 434. This determination is as to whether or not the count of the y counter is less than N. If the answer to this question is "yes", then the program proceeds to the point 436 where the y counter is incremented by one step and then to the point 406. Otherwise, the program proceeds to the end point 438.

Thus, the buffers XCB and YCB eventually store values which indicate the x and y coordinates of the center position of the driver's iris. In addition, the maximum value Δmax eventually stored in the computer memory is equal to the brightness difference related to the center of the driver's iris and it is used to detect whether the driver's eye is open or closed by a comparison with an appropriate threshold value Th. That is, the driver's eye is open when $\Delta\text{max} > Th$ and closed when $\Delta\text{max} \leq Th$.

Figure 10:
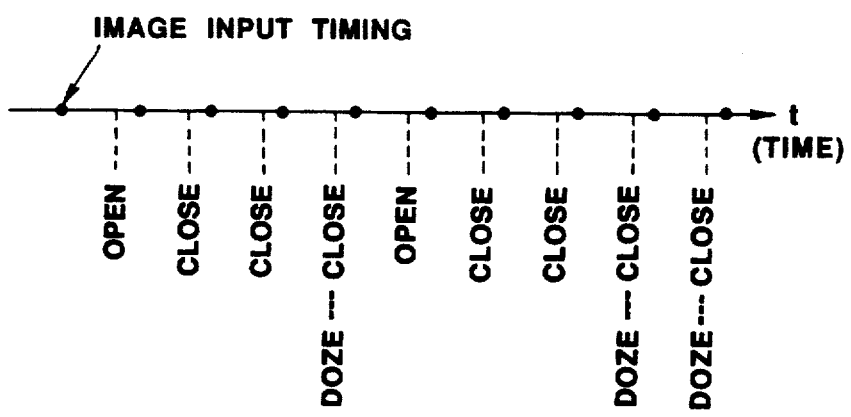
FIG. 10 is a diagram used in explaining the principles of the driver's doze detection.

This can be utilized to detect a driver's doze and inattentive driving. The driver's doze may be detected when the number of times the closure of the driver's eye is detected consecutively exceeds a predetermined value (in the illustrated case three), as shown in FIG. 10. The driver's inattentive driving will be detected when the number of times the closure of only one of the driver's eye is detected consecutively exceeds a predetermined value.

According to the invention, the X coordinates of the first and second rectangular regions W1 and W2 are calculated based upon the X coordinates of the initial and final pixels of a line segmen representing the longest width of the face. Therefore, the accuracy with which the apparatus detects the eye positions is free from shadows on the inputted image. In addition, the Y coordinates of the first and second rectangular regions W1 and W2 can be detected by scanning a small portion of the binary coded image. This is effective to reduce the image processing time required to detect the eye positions.

What is claimed is:

1. An eye position detecting apparatus comprising:
   image input means for inputting an image of a face including eyes; and
   a microcomputer, the microcomputer including:
   image converting means for converting the inputted image into a binary coded image formed by an array of pixels, each of the pixels having a first value indicating a black pixel or a second value indicating a white pixel, and each being located at a position specified by coordinates (X,Y); and
   detecting means for processing the binary coded image to detect first and second rectangular regions including image portions representing the eyes, respectively, each of the first and second rectangular regions being specified by two X coordinates, the detecting means including:
   first means for scanning the binary coded image in a series of horizontal scan lines to detect the X and Y coordinates of initial and final pixels of a line segment representing the longest width of the face;
   second means for calculating the X coordinates of each of the first and second rectangular regions based upon the detected X coordinates of the initial and final pixels;

third means for scanning an image portion above the line segment to detect the Y coordinate of a lowermost one of pixels forming black image portions; and fourth means for calculating the Y coordinates of the first and second rectangular regions based upon the detected Y coordinate of the lowermost pixel.

2. The eye position detecting apparatus as claimed in claim 1, wherein the first means includes means for detecting the X and Y coordinates of the initial and final pixels of a longest white line segment formed by a greatest number of consecutive white pixels arranged along one of the horizontal scan lines.

3. The eye position detecting apparatus as claimed in claim 2, wherein the first means includes means for producing an inhibitory signal when the number of consecutive white pixels forming a line segment is greater than a predetermined value, and means responsive to the inhibitory signal for preventing the line segment from being detected as the longest line segment.

4. The eye position detecting apparatus as claimed in claim 1, wherein the third means scans the binary coded image upward in a series of vertical scan lines over a range of $X1 \leq X \leq X2$ and $0 \leq Y \leq YL$ where X1 and X2 are the calculated X coordinates of each of the first and second rectangular regions and YL is the detected Y coordinate of the line segment.

5. The eye position detecting apparatus as claimed in claim 4, wherein each vertical scan line is arranged for a predetermined number of pixels.

6. The eye position detecting apparatus as claimed in claim 4, wherein the third means includes means for detecting the Y coordinate of a lowermost one of black pixels forming a lower black image portion and the Y coordinate of a lowermost one of black pixels forming an upper black area image portion, means for detecting an image portion representing a spectacle frame, and wherein the fourth means includes means for calculating the Y coordinates of the first and second rectangular regions based upon the detected Y coordinate of the lowermost pixel of the upper black image portion.

7. The eye position detecting apparatus as claimed in claim 6, wherein the means for detecting an image portion representing a spectacle frame includes means for scanning the binary coded image in horizontal scan lines between Y coordinates of the lowermost pixels of the upper and lower black image portions to detect black pixels, and means for detecting the spectacle frame when a predetermined number of black pixels are detected.

8. The eye position detecting means as claimed in claim 6, wherein the third means includes for detecting one of the lower and upper black image portions when at least two consecutive black pixels exist on one of the vertical scan lines.

9. The eye position detecting apparatus according to claim 1, wherein said image input means includes a source of light intermittently irradiating said face, a timing circuit controlling actuation of said source of light, a video camera providing a video signal of said irradiated face, and an analog-to-digital converter receiving said video signal and converting it into digital form.

10. An eye position detecting apparatus comprising:
image input means for inputting an image of a face including eyes;
image converting means for converting the inputted image into a binary coded image formed by an array of pixels, each of the pixels having a first value indicating a black pixel or a second value indicating a white pixel, and each being located at a position specified by coordinates (X,Y); and
a microcomputer including detecting means for processing the binary coded image to detect first and second rectangular regions including image portions representing the eyes, respectively, each of the first and second rectangular regions being specified by two X coordinates and two Y coordinates, the detecting means including:
first means for scanning the binary coded image in a series of horizontal scan lines to detect the X and Y coordinates of initial and final pixels of a line segment representing the longest width of the face;
second means for calculating the X coordinates of each of the first and second rectangular regions based upon the detected X coordinates of the initial and final pixels;
third means for scanning an image portion above the line segment to detect the Y coordinate of a lowermost one of pixels forming black image portions; and
fourth means for calculating the Y coordinates of the first and second rectangular regions based upon the detected Y coordinate of the lowermost pixel.

11. The eye position detecting apparatus as claimed in claim 10, wherein the first means includes means for detecting the X and Y coordinates of the initial and final pixels of a longest white line segment formed by a greatest number of consecutive white pixels arranged along one of the horizontal scan lines.

12. The eye position detecting apparatus as claimed in claim 11, wherein the first means includes means for producing an inhibitory signal when the number of consecutive white pixels forming a line segment is greater than a predetermined value, and means responsive to the inhibitory signal for preventing the line signal from being detected as the longest line segment.

13. The eye position detecting apparatus as claimed in claim 10, wherein the third means scans the binary coded image upward in a series of vertical scan lines over a range of $X1 \leq X \leq X2$ and $0 \leq Y \leq YL$ where X1 and X2 are the calculated X coordinates of each of the first and second rectangular regions and YL is the detected Y coordinate of the line segment.

14. The eye position detecting apparatus as claimed in claim 13, wherein each vertical scan line is arranged for a predetermined number of pixels.

15. The eye position detecting apparatus as claimed in claim 13, wherein the third means includes means for detecting the Y coordinate of a lowermost one of black pixels forming a lower black image portion and the Y coordinate of a lowermost one of black pixels forming an upper black area image portion, means for detecting an image portion representing a spectacle/frame, and wherein the fourth means includes means for calculating the Y coordinates of the first and second rectangular regions based upon the detected Y coordinate of the lowermost pixel of the upper black image portion.

16. The eye position detecting apparatus as claimed in claim 15, wherein the means for detecting an image portion representing a spectacle frame includes means for scanning the binary coded image in horizontal scan lines between Y coordinates of the lowermost pixels of the upper and lower black image portions to detect black pixels, and means for detecting the spectacle frame when a predetermined number of black pixels are detected.

17. The eye position detecting means as claimed in claim 15, wherein the third means includes means for detecting one of the lower and upper black image portions when at least two consecutive black pixels exist on one of the vertical scan lines.

18. The eye position detecting apparatus according to claim 10, wherein said image input means includes a source of light intermittently irradiating said face, a timing circuit controlling actuation of said source of light, a video camera providing a video signal of said irradiated face, and an analog-to-digital converter receiving said video signal and converting it into digital form.

19. An eye position detecting apparatus comprising:
image input means for inputting an image of a face including eyes; and
a microcomputer, the microcomputer including:
image converting means for converting the inputted image into a binary coded image formed by an array of pixels, each of the pixels having a first value indicating a black pixel or a second value indicating a white pixel, and each being located at a position specified by coordinates (X,Y); and
detecting means for processing the binary coded image to detect a rectangular region including an image portion representing one of the eyes, the rectangular region being specified by two X coordinates and two Y coordinates, the detecting means including:
first means for scanning the binary coded image in a series of horizontal scan lines to detect the X and Y coordinates of initial and final pixels of a line segment representing the longest width of the face;
second means for calculating the X coordinates of the rectangular region based upon the detected X coordinates of the initial and final pixels;
third means for scanning an image portion above the line segment to detect the Y coordinate of a lowermost one of pixels forming black image portions; and
fourth means for calculating the Y coordinates of the rectangular region based upon the detected Y coordinate of the lowermost pixel.

20. The eye position detecting apparatus as claimed in claim 19, wherein the first means includes means for detecting the X and Y coordinates of the initial and final pixels of a longest white line segment formed by a greatest number of consecutive white pixels arranged along one of the horizontal scan lines.

21. The eye position detecting apparatus as claimed in claim 20, wherein the first means includes means for producing an inhibitory signal when the number of consecutive white pixels forming a line segment is greater than a predetermined value, and means responsive to the inhibitory signal for preventing the line segment from being detected as the longest line segment.

22. The eye position detecting apparatus as claimed in claim 19, wherein the third means scans the binary coded image upward in a series of vertical scan lines over a range of $X1 \leq X \leq X2$ and $0 \leq Y \leq YL$ where X1 and X2 are the calculated X coordinates of the rectangular region and YL is the detected Y coordinate of the line segment.

23. The eye position detecting apparatus as claimed in claim 22, wherein each vertical scan line is arranged for a predetermined number of pixels.

24. The eye position detecting apparatus as claimed in claim 22, wherein the third means includes means for detecting the Y coordinate of a lowermost one of black pixels forming a lower black image portion and the Y coordinate of a lowermost one of black pixels forming an upper black area image portion, means for detecting an image portion representing a spectacle frame, and wherein the fourth means includes means for calculating the Y coordinate of the rectangular region based upon the detected Y coordinate of the lowermost pixel of the upper black image portion.

25. The eye position detecting apparatus as claimed in claim 24, wherein the means for detecting an image portion representing a spectacle frame includes means for scanning the binary coded image in horizontal scan lines between Y coordinates of the lowermost pixels of the upper and lower black image portions to detect black pixels, and means for detecting the spectacle frame when a predetermined number of black pixels are detected.

26. The eye position detecting means as claimed in claim 24, wherein the third means includes means for detecting one of the lower and upper black image portions when at least two consecutive black pixels exist on one of the vertical scan lines.

27. The eye position detecting apparatus according to claim 19, wherein said image input means includes a source of light intermittently irradiating said face, a timing circuit controlling actuation of said source of light, a video camera providing a video signal of said irradiated face, and an analog-to-digital converter receiving said video signal and converting it into digital form.

28. An eye position detecting apparatus comprising:
image input means for inputting an image of a face including eyes;
image converting means for converting the inputted image into a binary coded image formed by an array of pixels, each of the pixels having a first value indicating a black pixel or a second value indicating a white pixel, and each being located at a position specified by coordinates (X,Y); and
a microcomputer including detecting means for processing the binary coded image to detect a rectangular region including image portions representing one of the eyes, the rectangular region being specified by two X coordinates and two Y coordinates, the detecting means including:
first means for scanning the binary coded image in a series of horizontal scan lines to detect the X and Y coordinates of initial and final pixels of a line segment representing the longest width of the face;
second means for calculating the X coordinates of the rectangular region based upon the detected X coordinates of the initial and final pixels;
third means for scanning an image portion above the line segment to detect the Y coordinates of a lowermost one of pixels forming black image portions; and
fourth means for calculating the Y coordinates of the rectangular region based upon the detected Y coordinate of the lowermost pixel.

29. The eye position detecting apparatus as claimed in claim 28, wherein the first means includes means for detecting the X and Y coordinates of the initial and final pixels of a longest white line segment formed by a greatest number of consecutive white pixels arranged along one of the horizontal scan lines.

30. The eye position detecting apparatus as claimed in claim 29, wherein the first means includes means for producing an inhibitory signal when the number of consecutive white pixels forming a line segment is greater than a predetermined value, and means responsive to the inhibitory signal for preventing the line segment from being detected as the longest line segment.

31. The eye position detecting apparatus as claimed in claim 28, wherein the third means scans the binary coded image upward in a series of vertical scan lines over a range of $X1 \leq X \leq X2$ and $0 \leq Y \leq YL$ where $X1$ and $X2$ are the calculated X coordinates of the rectangular region and $YL$ is the detected Y coordinate of the line segment.

32. The eye position detecting apparatus as claimed in claim 31, wherein each vertical scan line is arranged for a predetermined number of pixels.

33. The eye position detecting apparatus as claimed in claim 31, wherein the third means includes means for detecting the Y coordinate of a lowermost one of black pixels forming a lower black image portion and the Y coordinate of a lowermost one of black pixels forming an upper black area image portion, means for detecting an image portion representing a spectacle frame, and wherein the fourth means includes means for calculating the Y coordinate of the rectangular region based upon the detected Y coordinate of the lowermost pixel of the upper black image portion.

34. The eye position detecting apparatus as claimed in claim 33, wherein the means for detecting an image portion representing a spectacle frame includes means for scanning the binary coded image in horizontal scan lines between Y coordinates of the lowermost pixels of the upper and lower black image portions to detect black pixels, and means for detecting the spectacle frame when a predetermined number of black pixels are detected.

35. The eye position detecting means as claimed in claim 33, wherein the third means includes means for detecting one of the lower and upper black image portions when at least two consecutive black pixels exist on one of the vertical scan lines.

36. The eye position detecting apparatus according to claim 28, wherein said image input means includes a source of light intermittently irradiating said face, a timing circuit controlling actuation of said source of light, a video camera providing a video signal of said irradiated face, and an analog-to-digital converter receiving said video signal and converting it into digital form.

* * * * *